(12) United States Patent
Dybiec

(10) Patent No.: US 11,857,151 B2
(45) Date of Patent: Jan. 2, 2024

(54) SYSTEMS AND METHODS FOR STANDALONE ENDOSCOPIC OBJECTIVE IMAGE ANALYSIS

(71) Applicant: STERIS Instrument Management Services, Inc., Birmingham, AL (US)

(72) Inventor: Maciej Dybiec, Cooper City, FL (US)

(73) Assignee: STERIS Instrument Management Services, Inc., Birmingham, AL (US)

(*) Notice: Subject to any disclaimer, the term of this patent is extended or adjusted under 35 U.S.C. 154(b) by 0 days.

(21) Appl. No.: 16/129,519

(22) Filed: Sep. 12, 2018

(65) Prior Publication Data

US 2020/0084368 A1    Mar. 12, 2020

(51) Int. Cl.
| | |
|---|---|
| H04N 5/20 | (2006.01) |
| G06T 7/174 | (2017.01) |
| A61B 1/00 | (2006.01) |
| G06T 5/00 | (2006.01) |
| G06T 7/00 | (2017.01) |
| A61B 1/04 | (2006.01) |

(Continued)

(52) U.S. Cl.
CPC ............ *A61B 1/00009* (2013.01); *A61B 1/04* (2013.01); *G06T 5/003* (2013.01); *G06T 5/006* (2013.01); *G06T 7/0012* (2013.01); *H04N 23/67* (2023.01); *G06T 5/005* (2013.01); *G06T 7/174* (2017.01); *G06T 2207/10068* (2013.01); *G06T 2207/20221* (2013.01); *G06T 2207/30168* (2013.01); *H04N 23/6845* (2023.01); *H04N 23/951* (2023.01)

(58) Field of Classification Search
CPC ....... G06T 5/006; G06T 7/0012; G06T 7/174; G06T 5/005; G06T 2207/10068; G06T 2207/20221; G06T 2207/30168; A61B 1/00009; H04N 5/23232; H04N 5/23277
See application file for complete search history.

(56) References Cited

U.S. PATENT DOCUMENTS 5,648,652 A * 7/1997 Sekiya ................. G02B 7/36
                                                250/201.7
5,828,500 A * 10/1998 Kida ................. G01M 11/02
                                                359/799

(Continued)

FOREIGN PATENT DOCUMENTS

| | | |
|---|---|---|
| JP | 2002-071513 A | 3/2002 |
| JP | 2003-329543 A | 11/2003 |
| WO | WO2009146297 A1 | 12/2009 |

*Primary Examiner* — Mushfikh I Alam
(74) *Attorney, Agent, or Firm* — C. Brandon Browning; Ilya S. Mirov; Maynard Nexsen PC

(57) ABSTRACT

An objective of an endoscope can be evaluated by collecting a series of differently focused images and digitally stitching them together to obtain a final image for the endoscope that can be then evaluated. Movable optics and/or a camera can be used to collect the series of differently focused images. Image processing algorithms can be used to evaluate the collected images in terms of image sharpness and identify the areas at which each image is in relatively good focus. Once the areas of good focus are identified, the image processing algorithms can extract the areas of good focus. The digital stitching algorithms can be used to assemble the extracted areas of good focus to form a final image where most of the target scene should be in focus. The final image is then reviewed to determine the acceptability of the objective.

22 Claims, 8 Drawing Sheets

(51) Int. Cl.
*H04N 23/67* (2023.01)
*H04N 23/951* (2023.01)
*H04N 23/68* (2023.01)

(56) References Cited

U.S. PATENT DOCUMENTS

| | | | | |
|---|---|---|---|---|
| 5,986,271 | A * | 11/1999 | Lazarev | A61B 1/043 250/458.1 |
| 7,009,775 | B2 * | 3/2006 | Togino | G02B 5/10 353/38 |
| 7,375,745 | B2 | 5/2008 | Rai et al. | |
| 7,892,165 | B2 * | 2/2011 | Nakamura | A61B 1/045 600/109 |
| 8,180,101 | B2 * | 5/2012 | Sun | G01B 11/2504 348/180 |
| 8,223,193 | B2 * | 7/2012 | Zhao | G01D 1/00 348/45 |
| 8,681,224 | B2 * | 3/2014 | Mallon | G01M 11/0264 348/180 |
| 9,224,193 | B2 * | 12/2015 | Tsujimoto | G06T 5/003 |
| 9,324,172 | B2 * | 4/2016 | Wu | H04N 5/23229 |
| 9,438,897 | B2 * | 9/2016 | Barreto | H04N 17/002 |
| 2003/0060681 | A1 * | 3/2003 | Yokota | A61B 1/00022 600/117 |
| 2004/0044271 | A1 * | 3/2004 | Stone | A61B 1/00096 600/182 |
| 2005/0052559 | A1 | 3/2005 | Hayaishi | |
| 2006/0029284 | A1 * | 2/2006 | Stewart | G06T 7/13 348/E5.045 |
| 2006/0056731 | A1 | 3/2006 | Bouk et al. | |
| 2008/0137938 | A1 * | 6/2008 | Zahniser | G02B 21/244 382/133 |
| 2008/0281556 | A1 * | 11/2008 | Matsuzawa | G01M 11/0228 702/155 |
| 2009/0148062 | A1 * | 6/2009 | Gabso | G06T 5/20 382/266 |
| 2009/0220131 | A1 * | 9/2009 | Cinquin | G06K 9/00201 382/128 |
| 2009/0237498 | A1 * | 9/2009 | Modell | A61B 1/00165 348/65 |
| 2010/0014780 | A1 | 1/2010 | Kalayeh | |
| 2010/0149183 | A1 * | 6/2010 | Loewke | G06K 9/00134 345/424 |
| 2010/0272356 | A1 * | 10/2010 | Hong | G06T 7/0002 382/170 |
| 2011/0069160 | A1 * | 3/2011 | Ning | G02B 13/04 348/65 |
| 2011/0255759 | A1 | 10/2011 | Nishimura et al. | |
| 2012/0069167 | A1 * | 3/2012 | Liu | A61B 6/584 348/65 |
| 2013/0023730 | A1 * | 1/2013 | Kitamura | A61B 1/00009 600/104 |
| 2013/0046137 | A1 * | 2/2013 | Zhao | A61B 1/00181 600/102 |
| 2013/0217965 | A1 * | 8/2013 | Sasamoto | G02B 7/08 600/109 |
| 2014/0015856 | A1 | 1/2014 | Xiao et al. | |
| 2014/0210972 | A1 * | 7/2014 | On | A61B 1/00188 348/65 |
| 2014/0333750 | A1 * | 11/2014 | Zhuang | G02B 21/18 348/79 |
| 2015/0009357 | A1 * | 1/2015 | Seibel | A61B 1/00172 348/222.1 |
| 2015/0009492 | A1 | 1/2015 | Frese et al. | |
| 2015/0036027 | A1 * | 2/2015 | Winterot | H04N 5/23296 348/240.99 |
| 2015/0045619 | A1 * | 2/2015 | Kumar | A61B 1/00009 600/109 |
| 2015/0112126 | A1 * | 4/2015 | Popovic | A61F 2/062 600/36 |
| 2015/0208904 | A1 | 7/2015 | Yoon et al. | |
| 2015/0250380 | A1 * | 9/2015 | Ikeda | A61B 1/00194 600/111 |
| 2016/0320606 | A1 * | 11/2016 | Togino | G03B 35/10 |
| 2016/0338576 | A1 * | 11/2016 | Namii | G02B 23/2407 |
| 2016/0367148 | A1 * | 12/2016 | Froloff | A61B 5/0084 |
| 2017/0003493 | A1 * | 1/2017 | Zhao | G02B 23/243 |
| 2017/0199371 | A1 * | 7/2017 | Williamson | H04N 5/332 |
| 2017/0367561 | A1 * | 12/2017 | Park | A61B 1/00006 |
| 2018/0020152 | A1 * | 1/2018 | Kokubu | H04N 5/23212 |
| 2018/0368656 | A1 * | 12/2018 | Austin | A61B 1/0005 |
| 2020/0008660 | A1 * | 1/2020 | Uchida | A61B 1/00188 |
| 2020/0116990 | A1 * | 4/2020 | Sangu | G02B 27/10 |
| 2021/0137358 | A1 * | 5/2021 | Eguchi | A61B 1/00009 |

* cited by examiner

SYSTEMS AND METHODS FOR STANDALONE ENDOSCOPIC OBJECTIVE IMAGE ANALYSIS

BACKGROUND

The present application relates to analyzing images produced by an objective of an endoscope.

Objective image quality can be a key factor when evaluating overall endoscope performance. Thus, during the development or repair process for an objective of an endoscope, there is a continuing need for the ability to "look through" the objective of an endoscope to see the image provided by the objective. However, the objective is an optical component that can be very hard to evaluate standing alone (i.e., separate or apart from the endoscope) because the image that is formed by an objective is strongly over corrected (i.e., the plane in which the image is sharp is strongly curved) and for the "naked" eye of a user, only a small portion of the image can be in focus at any given time.

Currently, to properly check the objective of an endoscope, the objective has to be mounted in the endoscope and the entire optical system of the endoscope is used during the test image evaluation. The requirement to mount the objective in the endoscope assembly when evaluating the objective can be very cumbersome, expensive and time consuming, especially if the objective is determined to deliver inferior image quality and has to be remanufactured. The need to include the entire optical system of the endoscope during testing results from the endoscope being a compound optical device. Compound optical devices create many intermediate images of the object that are strongly over or under corrected before the final image is provided by the device to the pupil of a viewer's eye or the optical coupler of a camera.

SUMMARY

The present application generally pertains to evaluating an image delivered by an objective of an endoscope by capturing a series of intermediate images from the objective that have small areas in focus at different locations in space along the optical axis and then digitally stitching the intermediate images together to form the image for evaluation. The field curvature for images created by an objective of an endoscope can be very strong. The strong field curvature of the objective can result in a curved image plane from the objective that can be difficult to evaluate with a relatively simple imaging system.

The shifting of the focus point for the image plane along the optical axis (e.g., towards or away from the objective) can result in captured images having different areas in focus. For captured images that are digitally processed, areas of the corresponding images that are in relatively good focus can be identified and extracted or "cut out." The identification of areas in good focus can be done in many different ways. For example, areas of higher spatial frequencies may be identified as areas of good focus. In another example, sharpness and/or edge detection algorithms may be employed and the intensity maxima from the algorithms may be identified as areas of good focus. Once the area of good focus is identified, the image (or just the area in good focus) can be stored in the memory and the image capture device (e.g., a camera) can be moved to the next location for another area of the image to come into focus. The process of adjusting the focus point can be repeated 3-4 times (or more, if necessary) to get a full image area that is covered by the focused areas or portions.

The present application also pertains to a system and method for evaluating an objective by collecting a series of differently focused images and digitally stitching the images together in order to obtain a final image that corresponds to an image as seen through the objective. The system and method can use image processing and stitching algorithms to generate the final image. The system and method may also include some movable optics and a camera that can deliver a set of images used in later image processing. The collected images can be evaluated in terms of image sharpness and the areas at which each image is in relatively good focus. Once the good focus areas have been found, the areas can be extracted and used to form a final image where most of the target scene (e.g., the formed image of a target) should be in focus, thereby permitting the objective to be evaluated.

One advantage of the present application is that objective image quality analysis can be performed without the need for all of the optical systems of the endoscope to be present.

Another advantage of the present application is that the objective can be quickly evaluated thereby permitting a large volume of endoscopic objectives from large production batches or repair batches to receive quality inspections.

Other features and advantages of the present application will be apparent from the following more detailed description of the identified embodiments, taken in conjunction with the accompanying drawings which show, by way of example, the principles of the application.

BRIEF DESCRIPTION OF THE DRAWINGS

Wherever possible, the same reference numbers are used throughout the drawings to refer to the same or like parts.

DETAILED DESCRIPTION

Figure 1:
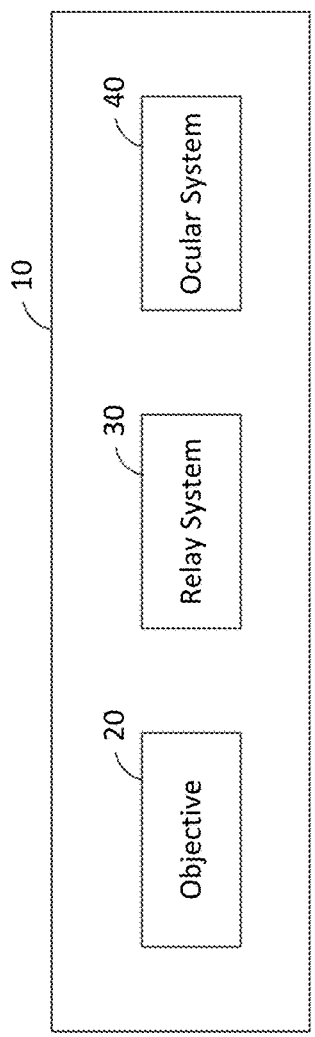
FIG. 1 shows a block diagram of an embodiment of an endoscope.

FIG. 1 shows an embodiment of an endoscope 10. The endoscope 10 can include a body encasing optical elements such as an objective 20, a relay system 30 and an ocular system 40. The objective 20 can be used to provide an image (e.g., reflected light) of a target (e.g., the object to be viewed) to the relay system 30. The objective 20 may include one or more lenses and/or other optical components. The relay system 30 can be used to transfer the image from the objective 20 to the ocular system 40. The relay system 30 can include one or more lenses and/or optical fibers to transfer the image from the objective 20. The ocular system 40 permits a user of the endoscope 10 to view the image from the objective 20. The ocular system 40 can include an eyepiece for direct viewing of the image and/or a camera system to capture and display the image. In some embodiments, the endoscope 10 may include one or more devices to transfer light from a light source to the target to illuminate the target.

Figure 2:
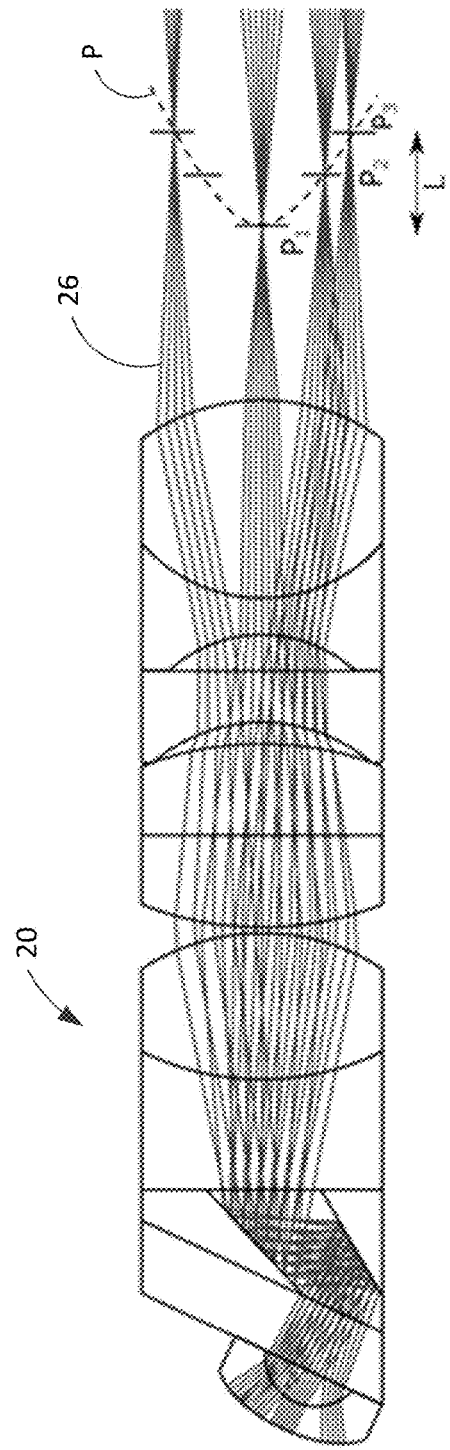
FIG. 2 shows an embodiment of an objective from an endoscope showing corresponding image planes from the objective.
Figure 3:
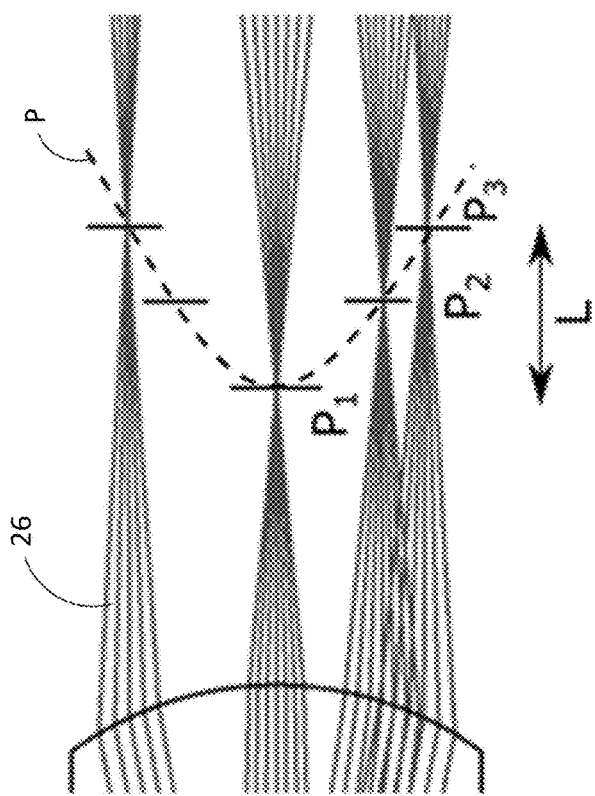
FIG. 3 show an enlarged view of the image planes from FIG. 2.

FIGS. 2 and 3 show an embodiment of the objective 20 from the endoscope 10 of FIG. 1. Light rays 26 passing through the objective 20 form a curved focal plane P in the image space. In the embodiment shown in FIGS. 2 and 3, four bundles of light rays 26 are shown passing through the objective 20, but more or less than four bundles of light rays may pass through the objective 20 in other embodiments. The curved focal plane P can be dissected by corresponding image planes P1-P3 over a distance L extending along the optical axis for the objective 20. While 3 image planes P1-P3 are shown in FIGS. 2 and 3, the focal plane P can be dissected by any number of image planes along the distance L.

Figure 4:
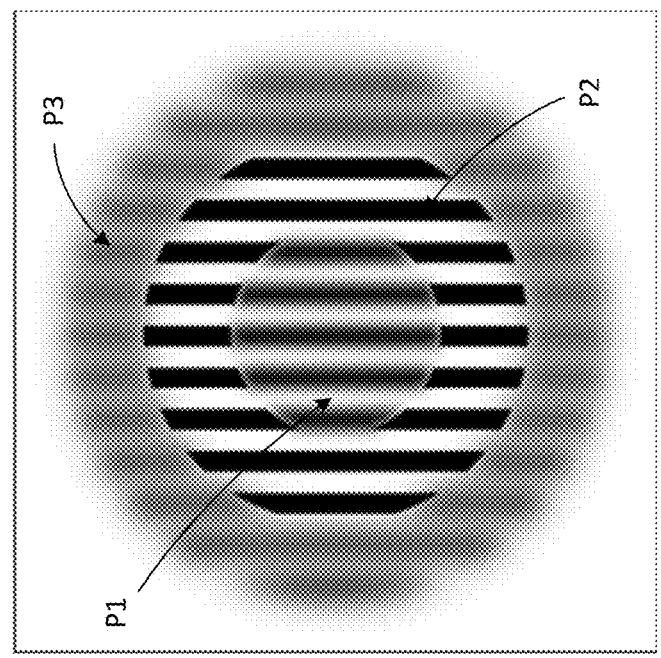
FIG. 4 shows an embodiment of an image captured from one of the image planes of FIG. 3.

For each image plane P1-P3, a portion of the image (from the object space) captured at the corresponding image plane can be in focus, while other portions of the image remain out of focus. FIG. 4 shows an embodiment of an image captured at image plane P2. As can be seen in FIG. 4, the portion of the image corresponding to image plane P2 is in focus, while the portions of the image corresponding to image planes P1 and P3 are out of focus.

Figure 5:
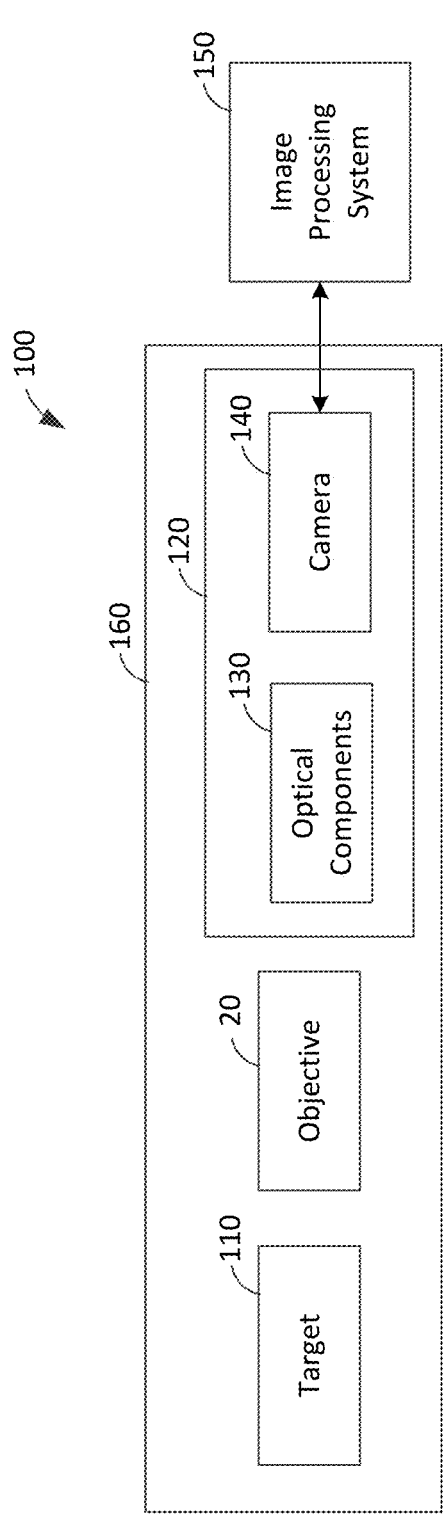
FIG. 5 shows a block diagram of an evaluation system for an endoscope.
Figure 6:
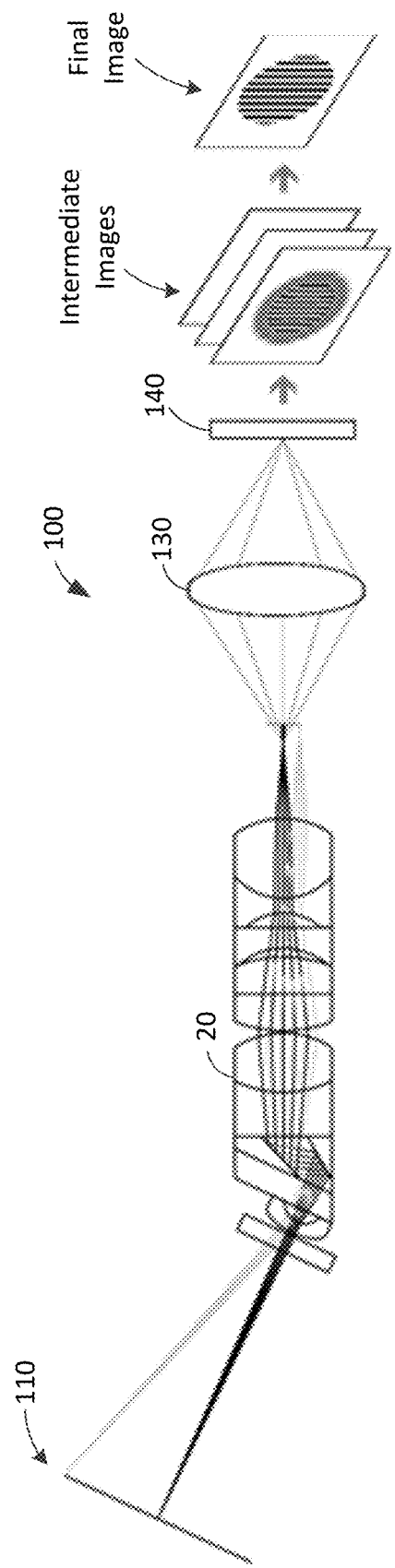
FIG. 6 shows an embodiment of a process using the evaluation system of FIG. 5.

FIGS. 5 and 6 show embodiments of an evaluation system used to evaluate objectives 20 from endoscopes 10. The evaluation system 100 can include a target 110, the objective 20 being evaluated or tested, an image capture system 120 and an image processing system 150. The image capture system 120 can include one or more optical components 130 (e.g., lenses, prisms, etc.) and/or a camera 140. In an embodiment, the camera 140 may be replaced by an image sensor (or sensor array) that can be used to capture images. The image sensor can be controlled and operated by the image processing system 150 in an embodiment.

In one embodiment, the target 110, the objective 20 being evaluated or tested and the image capture system 120 can be placed in a fixture or enclosure 160 that prevents or limits ambient light from reaching the camera 140. The target 110 can include features that allow in focus areas of captured images to be easily extracted. The target 110 can have a pattern that is uniform and of high contrast across the whole field of view. In one embodiment, the pattern for the target 110 can include a set of slanted (e.g., at a 45° angle) alternating black and white stripes with a width of about 0.5 mm (e.g., a "zebra" pattern). The use of a "zebra" pattern can be beneficial in image post processing and can be relatively easily reconstructed even on very blurry images. In an embodiment, the target 110 can be back illuminated to prevent parasitic reflections and the illumination level of the target 110 can be adjustable to obtain a desired image contrast from the camera 140.

The optical components 130 (sometimes referred to as pickup optics) includes movable optical elements that permit the objective image (i.e., the image formed by the objective 20) to be relayed onto the camera 140 from multiple image positions (e.g., image planes P1-P3) shifted along the longitudinal axis of the objective 20. The camera 140 can capture multiple intermediate images of the objective image from multiple image positions and provide the captured images to the image processing system 150. The image processing system 150 can evaluate the intermediate images from the camera 140 with image processing algorithms to extract image areas that are in focus. Once the intermediate images with corresponding in focus areas are extracted, the image processing system 150 can produce the final image used to evaluate the objective 20 by stitching together the extracted in focus areas from the intermediate images.

Figure 7:
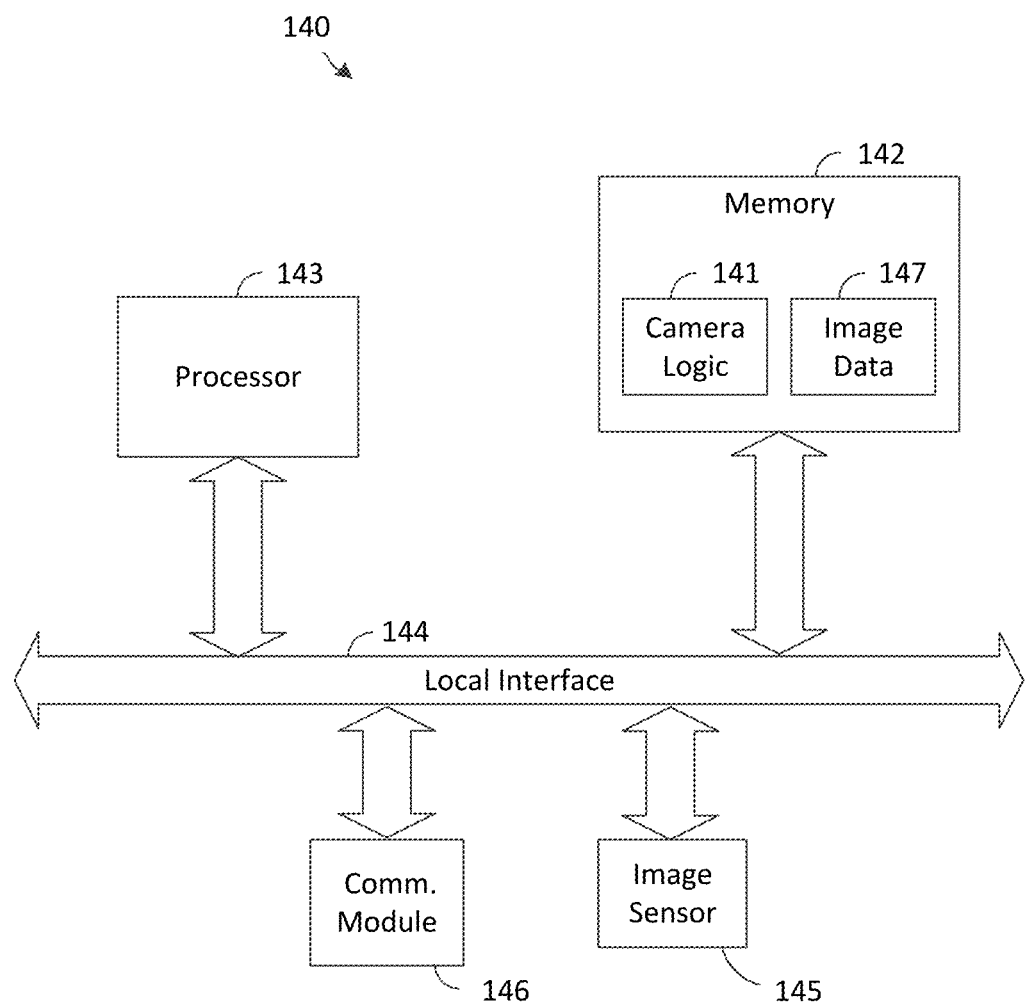
FIG. 7 is a block diagram of an embodiment of a camera used in the evaluation system of FIG. 5.

FIG. 7 shows an embodiment of a camera 140 that can be used with the evaluation system 100. The camera 140 shown in FIG. 7 can include logic 141, referred to herein as "camera logic," which may be implemented in software, firmware, hardware, or any combination thereof. In FIG. 7, the camera logic 141 is implemented in software and stored in memory 142. However, other configurations of the camera logic 141 are possible in other embodiments. The camera logic 141, when implemented in software, can be stored and transported on any computer-readable medium for use by or in connection with an instruction execution apparatus that can fetch and execute instructions.

The embodiment of the camera 140 shown in FIG. 7 can include at least one conventional processor 143, which can incorporate processing hardware for executing instructions stored in the memory 142. As an example, the processor 143 may include a central processing unit (CPU), a digital signal processor (DSP), and/or a graphic processing unit (GPU). The processor 143 can communicate to and drive the other elements within the camera 140 via a local interface 144, which can include at least one bus.

As shown by FIG. 7, the camera 140 can also include an image sensor 145 and a communication module 146. The image sensor 145 can be used to record, capture or obtain images from the objective 22 in the area surrounding or in proximity to the camera 140 (e.g., the image space). The communication module 146 can include a radio frequency (RF) radio or other device for communicating wirelessly with image processing system 150. In another embodiment, the communication module 146 may also include an interface permitting wired communication between the camera 140 and the image processing system 150.

The image sensor 145 can include one or more CCDs (charge coupled devices) and/or one or more active pixel sensors or CMOS (complementary metal-oxide-semiconductor) sensors. The images from the image sensor 145 can be stored as image data 147 in memory 142. The image data 147 can be stored in any appropriate file format, including, but not limited to, PNG (portable network graphics), JPEG (joint photographic experts group), TIFF (tagged image file format), MPEG (moving picture experts group), WMV (Windows media video), QuickTime and GIF (graphics interchange format).

From time-to-time, the camera logic 141 can be configured to transmit the image data 147 to the image processing system 150. The image data 147 may be analyzed by the image processing system 150 to determine if the objective 20 is acceptable for use in an endoscope 10. The image data 147 may be time-stamped based on the time indicated by a clock (not shown) in order to indicate when the image data 147 was obtained.

Figure 8:
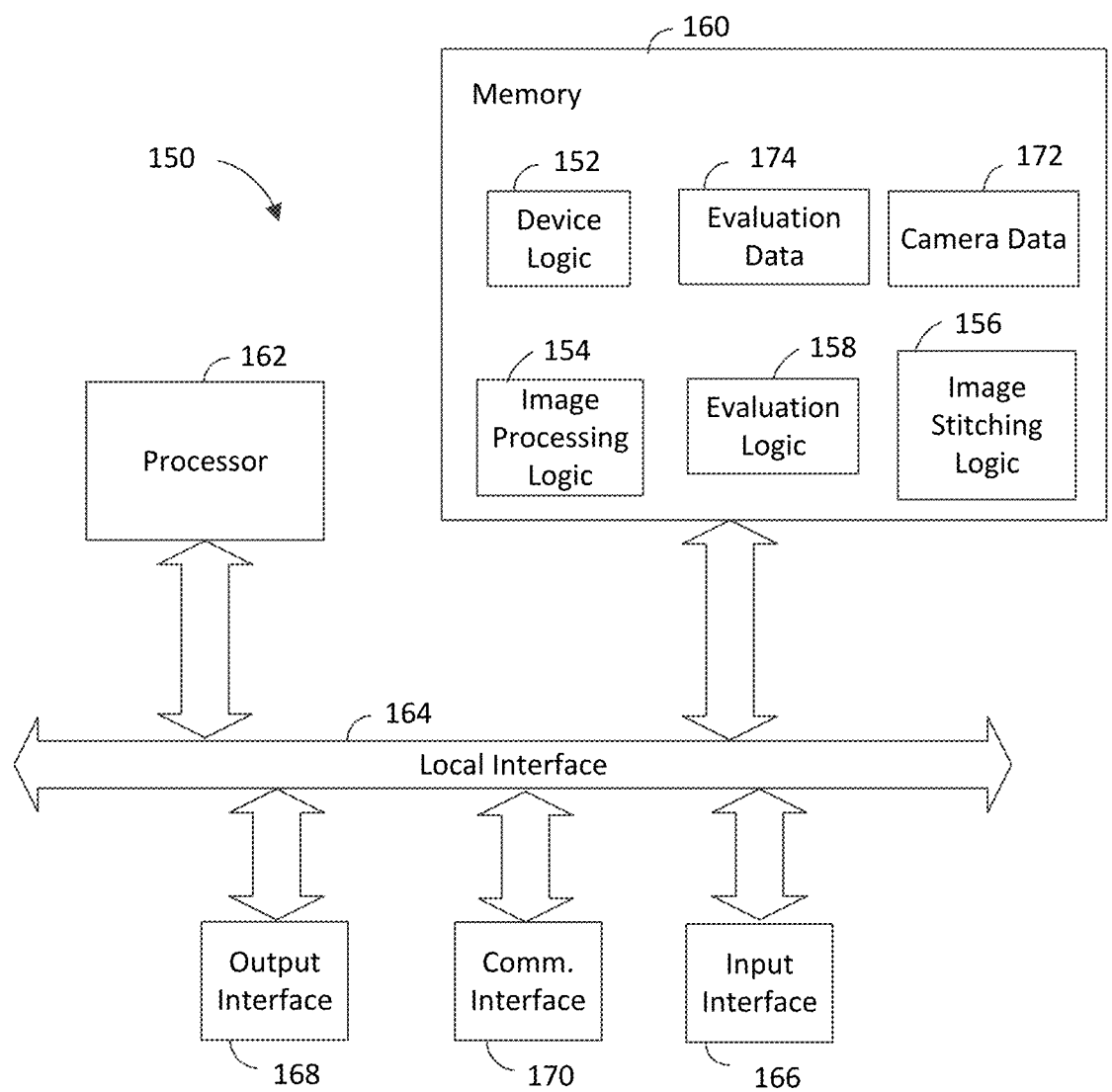
FIG. 8 is a block diagram of an embodiment of an image processing system used in the evaluation system of FIG. 5.

FIG. 8 shows an embodiment of the image processing system 150. The image processing system 150 may be implemented as one or more general or special-purpose computers, such as a laptop, hand-held (e.g., smartphone), desktop, or mainframe computer. The image processing system 150 can include logic 152, referred to herein as "device logic," for generally controlling the operation of the image processing system 150. The image processing system 150 also includes image processing logic 154 to determine the portions or areas of the images from the camera 140 that are in focus and image stitching control logic 156 to form an evaluation image (or final image) from the portions of the images determined to be in focus by the image processing logic 154. The image processing system 150 further includes evaluation logic 158 for processing and analyzing the evaluation image to determine the acceptability of the objective 22. The device logic 152, the image processing logic 154, the image stitching control logic 156 and the evaluation logic 158 can be implemented in software, hardware, firmware or any combination thereof. In the image processing system 150 shown in FIG. 8, the device logic 152, the image processing logic 154, the image stitching control logic 156 and the evaluation logic 158 are implemented in software and stored in memory 160 of the image processing system 150. Note that the device logic 152, the image processing logic 154, the image stitching control logic 156 and the evaluation logic 158, when implemented in software, can be stored and transported on any non-transitory computer-readable medium for use by or in connection with an instruction execution apparatus that can fetch and execute instructions.

The image processing system 150 can include at least one conventional processor 162, which has processing hardware for executing instructions stored in memory 160. As an example, the processor 162 may include a central processing unit (CPU), a digital signal processor (DSP), and/or a graphic processing unit (GPU). The processor 162 communicates to and drives the other elements within the image processing system 150 via a local interface 164, which can include at least one bus. Furthermore, an input interface 166, for example, a keypad, keyboard or a mouse, can be used to input data from a user of the image processing system 150, and an output interface 168, for example, a printer, monitor, liquid crystal display (LCD), or other display apparatus, can be used to output data to the user. Further, a communication interface 170 may be used to exchange data with the camera 140.

As shown by FIG. 8, camera data 172 and evaluation data 174 and can be stored in memory 160 at the image processing system 150. The camera data 172 can include image data 147 from the camera 140. The evaluation data 174 can include evaluation images generated by the image stitching logic 156 and/or information relating to the in focus areas of the images from the camera 140 determined by image processing logic 154. The camera data 172 and the evaluation data 174 can be used and/or analyzed by device logic 152, the image processing logic 154, the image stitching control logic 156 and the evaluation logic 158 to determine the acceptability of the objective 22 that generated the images.

Figure 9:
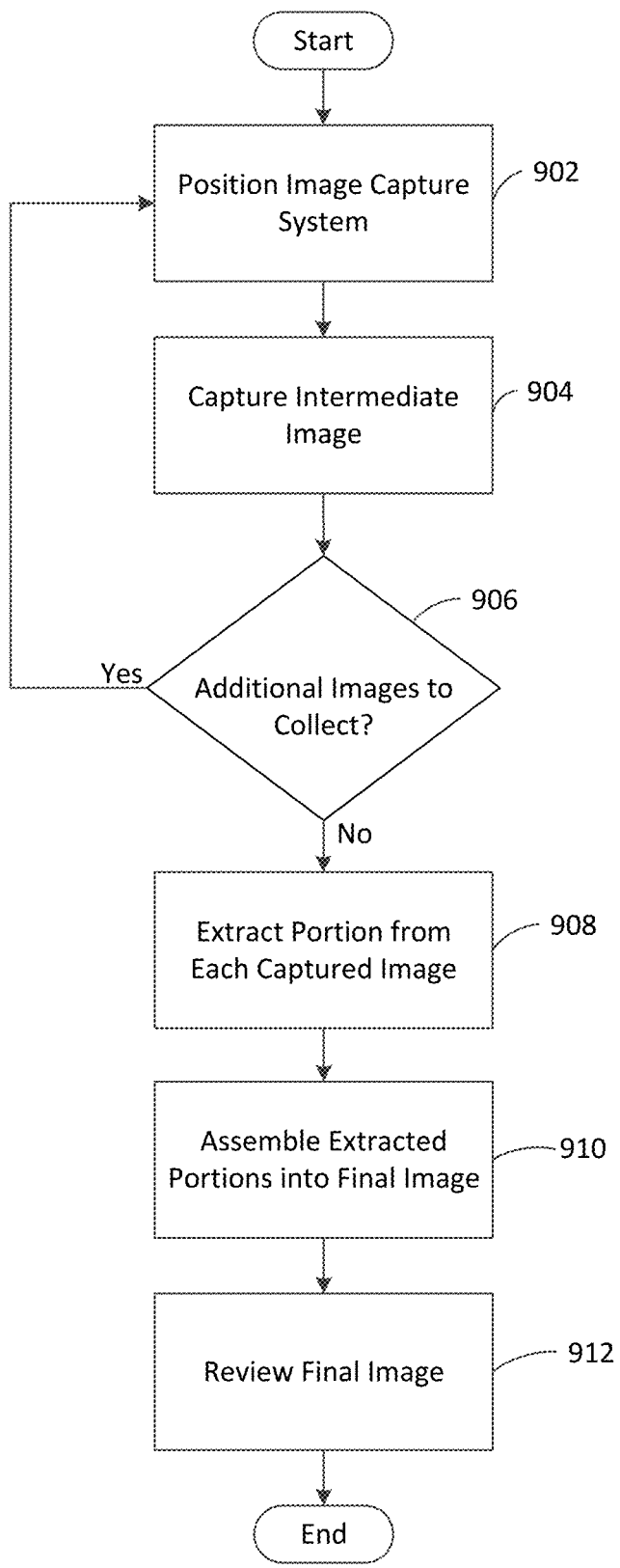
FIG. 9 is a flow diagram showing an embodiment of a process for evaluating an objective of an endoscope.

FIG. 9 is a flow chart showing an embodiment of a process for evaluating an objective 20 of an endoscope 10 with evaluation system 100. The objective 20 that is undergoing an evaluation can be positioned in the enclosure 160 of the system 100 with the target 110 such that the objective image formed by the objective 20 incorporates the target 110. The process of FIG. 9 can be used to evaluate objectives 20 as part of either a manufacturing process or a repair process for endoscopes 10.

Once the objective is positioned in the enclosure 160, the image capture system 120 can be positioned along the optical axis in the enclosure 160 (step 902) and an intermediate image can be captured (step 904). The positioning of the image capture system 120 in the enclosure can be used to obtain intermediate images where a particular portion or area of the intermediate image is in focus and the remaining portions of the intermediate image are out of focus. For each position of the image capture system 120 along the optical axis, the intermediate image can be captured. In an embodiment, the target illumination level may need to be adjusted for some of the axial positions of the image capture system 120 to achieve the best image contrast in the intermediate image. For example, intermediate images captured from an image plane at the center of the objective image can be much brighter in the center, while the intermediate images captured from an image plane that is in focus at the periphery of the objective image are darker due to natural vignetting within tested objective. Next, a determination can be made as to whether additional intermediate images need to be collected (step 906). If additional images are to be collected, the process returns to step 902 to position the image capture system 120 into another position. In one embodiment, a predetermined number of intermediate images of the objective image can be obtained from different positions along the focal plane of the objective 20 by adjusting the position of the image capture system 120. In another embodiment, the position of the objective 20 can be moved to obtain the predetermined number of intermediate images. Each of the intermediate images can have a different area or portion of the objective image in focus depending on where the intermediate image is captured (by the image capture system 120) with respect to the focal plane of the objective image.

Figure 10A:
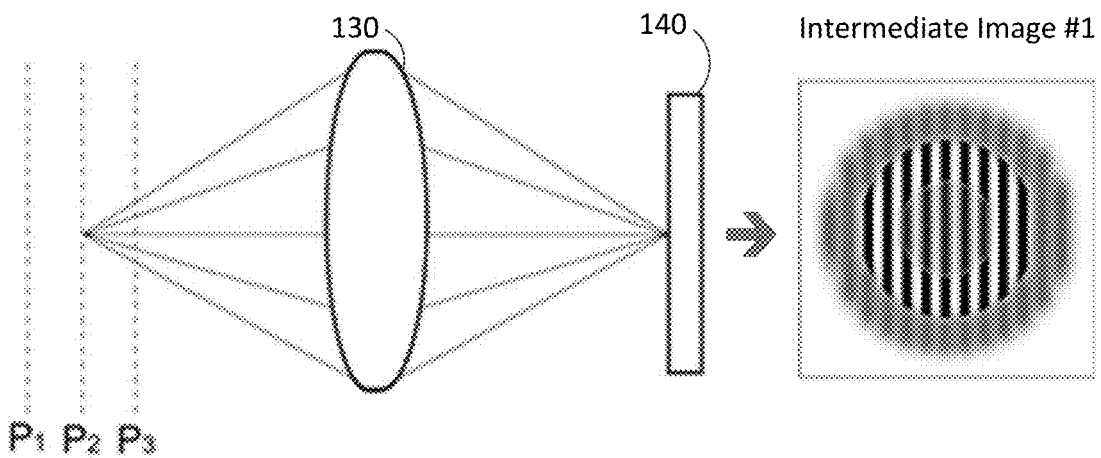
FIGS. 10A-10C show different positions for an embodiment of the image capture system.
Figure 10B:
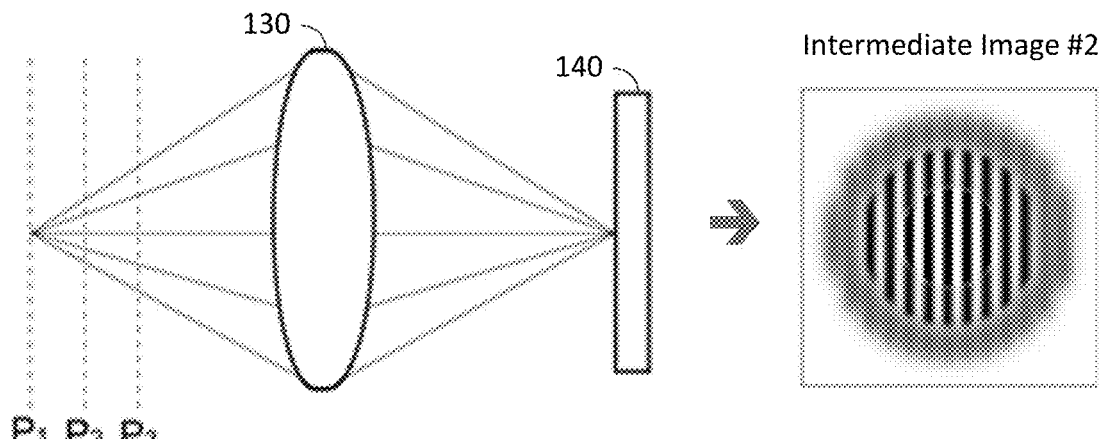
Figure 10C:
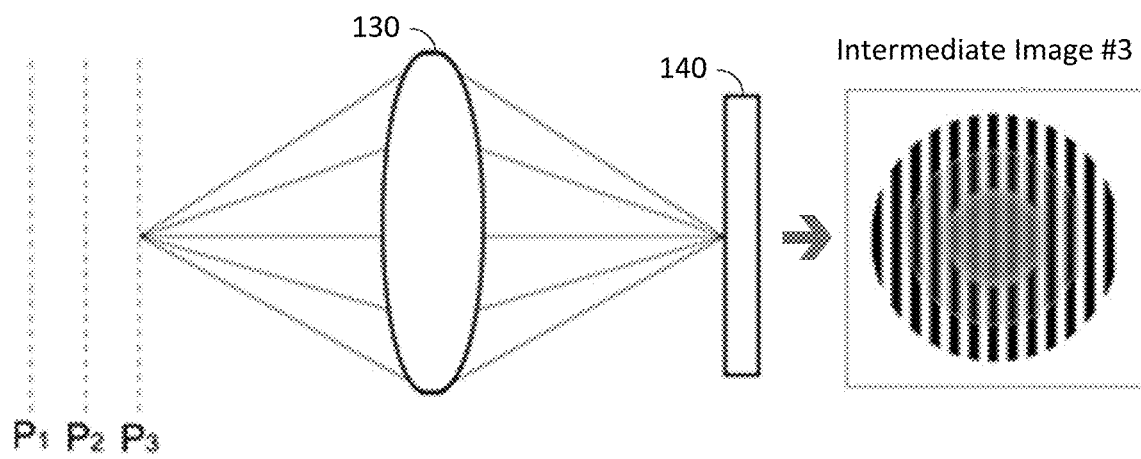

In one embodiment, the image capture system 120 can include optical components 130 and camera 140 that are moveable within fixture 160. The moveable optical components 130 and camera 140 can be fixed with respect to each other to maintain the image plane (sometimes referred to as the pick-up plane) in the best possible focus on the image sensor 145 of the camera 140. The optical components 130 and camera 140 can be mounted on a common assembly and move in tandem such that a substantially constant focal distance between the optical components 130 and the camera 140 is maintained and a substantially constant focal distance between the optical components 130 and image plane of the objective image being captured is maintained. The moveable optical components 130 and camera 140 can be refocused along the optical axis at different distances from the objective 20 to permit multiple intermediate images of the objective image to be captured. As shown in FIGS. 10A-10C, the optical components 130 and camera 140 can be positioned in different positions to capture intermediate images corresponding to image planes P1-P3. In FIG. 10A, the optical components 130 and camera 140 can be positioned to capture intermediate image #1. In intermediate image #1, the portion of the objective image corresponding to image plane P2 is in focus and the remaining portions of the objective image (e.g., the portions corresponding to image planes P1 and P3) are out of focus. In FIG. 10B, the optical components 130 and camera 140 can be positioned to capture intermediate image #2. In intermediate image #2, the portion of the objective image corresponding to image plane P1 is in focus and the remaining portions of the objective image (e.g., the portions corresponding to image planes P2 and P3) are out of focus. In FIG. 10C, the optical components 130 and camera 140 can be positioned to capture intermediate image #3. In intermediate image #3, the portion of the objective image corresponding to image plane P3 is in focus and the remaining portions of the objective image (e.g., the portions corresponding to image planes P1 and P2) are out of focus.

Figure 11A:
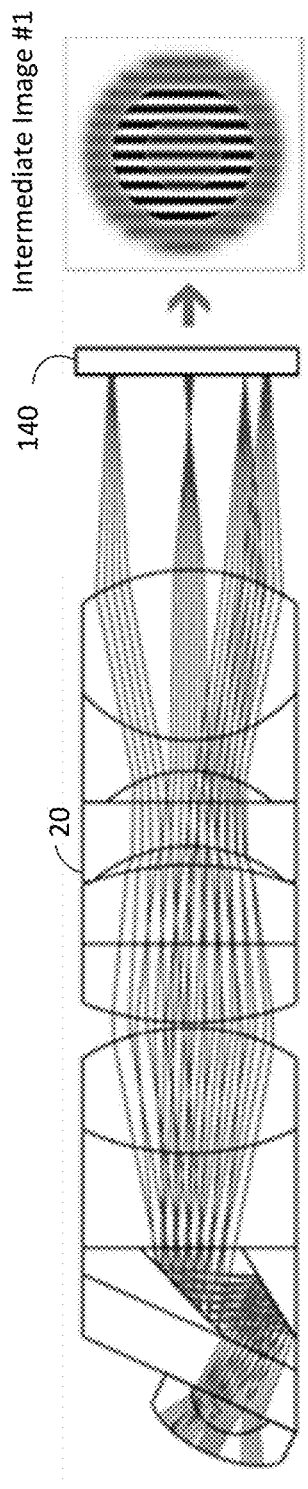
FIG. 11A-11C show different positions for another embodiment of the image capture system.
Figure 11B:
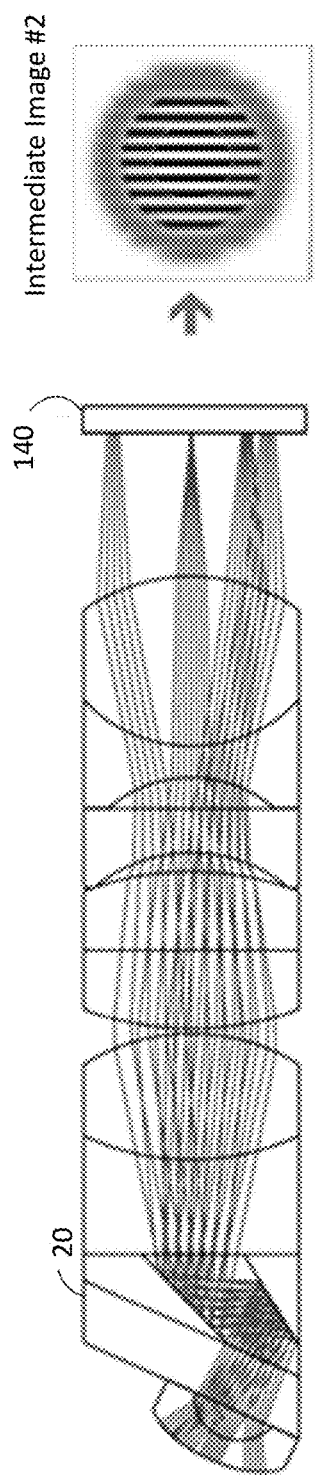
Figure 11C:
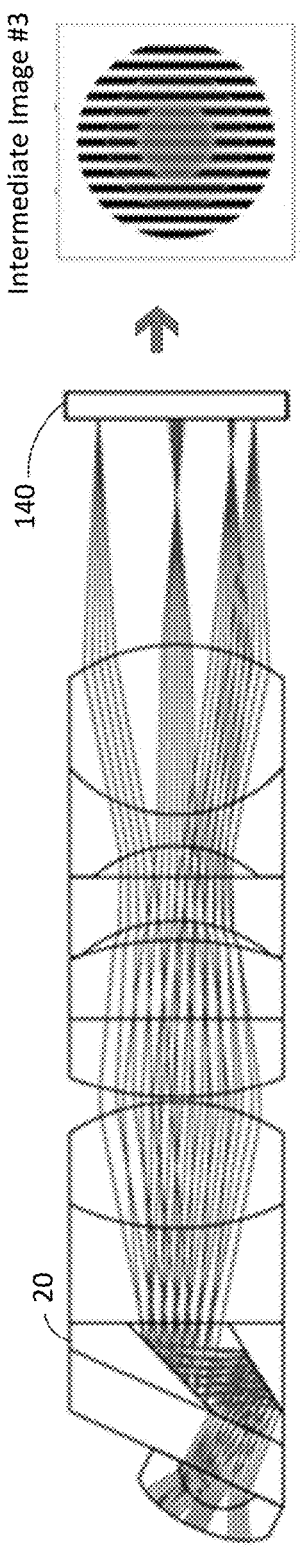

In another embodiment, the image capture system 120 may omit moveable optical components 130 (or have the optical components 130 in a fixed position) and just move camera 140. The moveable camera 140 can moved into different positions such that the image plane of the objective image being captured is in focus. As shown in FIGS. 11A-11C, the camera 140 can be positioned in different positions to capture intermediate images corresponding to image planes P1-P3. In FIG. 11A, the camera 140 can be positioned to capture intermediate image #1. In intermediate image #1, the portion of the objective image corresponding to image plane P2 is in focus and the remaining portions of the objective image (e.g., the portions corresponding to image planes P1 and P3) are out of focus. In FIG. 11B, the camera 140 can be positioned to capture intermediate image #2. In intermediate image #2, the portion of the objective image corresponding to image plane P1 is in focus and the remaining portions of the objective image (e.g., the portions corresponding to image planes P2 and P3) are out of focus. In FIG. 11C, the camera 140 can be positioned to capture intermediate image #3. In intermediate image #3, the portion of the objective image corresponding to image plane P3 is in focus and the remaining portions of the objective image (e.g., the portions corresponding to image planes P1 and P2) are out of focus.

Returning back to FIG. 9, once all of the intermediate images have been collected, each of the intermediate images can be processed with the image processing system 150 to extract a portion from each captured image (step 908). In an embodiment, when the intermediate images from respective image planes are collected (e.g., image planes P1-P3), the intermediate images can be evaluated in terms of image sharpness regions. While only three image planes (e.g., P1-P3) and three corresponding intermediate images are shown in the embodiments of FIGS. 10A-10C and FIGS. 11A-11C, additional image planes (e.g., 7-9 image planes and intermediate images) can be used in other embodiments. The number of image planes and intermediate images that may be required to generate a final image can depend on the strength of the correction for the objective 20 and the strength of the curvature for the focal plane of the objective image.

In one embodiment, the extracted portion of the intermediate image can correspond to the portion of the intermediate image that is in focus. Sharp or in focus portions of the intermediate image may be found using different techniques. For example, techniques involving edge and/or sharpness detection algorithms, local spatial frequency estimators, local gradients, etc. may be used. In one embodiment, Sobel matrix operators for local gradients was used. In another embodiment, the extracted portion of the intermediate image can correspond to a predetermined portion of the objective image that is related to the image plane being captured by the intermediate image.

The extracted portions of the intermediate images can be stitched (or assembled) together by the image processing system to form a final image (step 910). In one embodiment, if there are areas of the final image are not covered by any extracted portion from the intermediate images, additional intermediate images may be collected to guarantee full coverage of the final image. The final focused image can be used for the evaluation of the objective 20 being tested and can be used to find any imperfections in optical subcomponents or the assembly of the objective 20. The final image can correspond to the objective image provided by the objective 20. However, the final image can differ from the image that is formed by a fully assembled endoscope 10, when the rest of the endoscope optics are present. The slight difference in images can be due to a fact that some optical aberrations of the objective 20 may be corrected in the remaining part of the relay system 30 and the ocular system 40. The image processing system 150 can then review the final image (step 912) to determine the acceptability of the final image. If the acceptability of the final image can directly correspond to the acceptability of the objective 20 being evaluated. If the final image is acceptable, then the objective 20 is also acceptable. However, if the final image is not acceptable (or is rejected), then the objective 20 is also not acceptable and rejected.

Although the figures herein may show a specific order of method steps, the order of the steps may differ from what is depicted. Also, two or more steps may be performed concurrently or with partial concurrence. Variations in step performance can depend on the software and hardware systems chosen and on designer choice. All such variations are within the scope of the application. Software implementations could be accomplished with standard programming techniques, with rule based logic and other logic to accomplish the various connection steps, processing steps, comparison steps and decision steps.

It should be understood that the identified embodiments are offered by way of example only. Other substitutions, modifications, changes and omissions may be made in the design, operating conditions and arrangement of the embodiments without departing from the scope of the present application. Accordingly, the present application is not limited to a particular embodiment, but extends to various modifications that nevertheless fall within the scope of the application. It should also be understood that the phraseology and terminology employed herein is for the purpose of description only and should not be regarded as limiting.

What is claimed is:

1. A system to evaluate an objective of an endoscope, the system comprising:

an objective from an endoscope, the objective being apart from the endoscope and having an optical axis;

an image capture system configured to capture a plurality of intermediate images of a formed image from the objective, the image capture system being movable along the optical axis to capture the plurality of intermediate images, and the formed image from the endoscopic objective having a curved focal plane and each intermediate image of the plurality of intermediate images corresponding to a different image plane with respect to the optical axis taken from the curved focal plane; and an image processing system communicatively coupled to the image capture system to receive the plurality of intermediate images from the image capture system, the image processing system configured to extract at least one portion from each intermediate image of the plurality of intermediate images that corresponds to an in focus portion of the intermediate image, the image processing system configured to assemble the extracted portions from the plurality of intermediate images to form a final image, wherein the final image corresponds to the formed image from the objective, and wherein an evaluation of the final image by the image processing system determines acceptability of the objective, wherein the image capture system includes at least one optical component configured for relaying and focusing the formed image and curved focal plane, and wherein the image processing system is configured to reject the objective responsive to determining that the final image is not acceptable.

2. The system of claim 1, wherein the image capture system comprises a camera, the camera movable along the optical axis to capture the plurality of intermediate images.

3. The system of claim 2, wherein the at least one optical component is positioned directly between the camera and the objective and configured for relaying the formed image and curved focal plane onto the camera, wherein the at least one optical component is movable along the optical axis.

4. The system of claim 3, wherein the camera and the at least one optical component are configured to move in tandem.

5. The system of claim 1, wherein the image processing system is configured to identify the in focus portion of the intermediate image based on at least one of an area of higher spatial frequencies or intensity maxima from an edge detection algorithm.

6. The system of claim 1, wherein the in focus portion of each intermediate image of the plurality of intermediate images is based on the location of the image capture system along the optical axis.

7. The system of claim 1, further comprising a target, the target having at least one feature included in the formed image from the objective.

8. The system of claim 7, further comprises an enclosure, the target, the objective and the image capture system are positioned inside the enclosure, and wherein the enclosure is configured to prevent ambient light from reaching the image capture system.

9. A method of evaluating of an objective of an endoscope, the method comprising:
 forming an image of a target with an endoscope objective, wherein the objective is apart from the endoscope, the formed image including a curved focal plane;
 relaying the formed image onto a camera of an image capture system, wherein the relayed formed image includes the curved focal plane,
 acquiring with the image capture system, a plurality of intermediate images from the formed image at a plurality of positions along an optical axis of the objective, wherein each intermediate image of the plurality of intermediate images corresponds to a different image plane with respect to the optical axis taken from the curved focal plane;
 providing, by the image capture system, the plurality of intermediate images to an image processing system;
 extracting, by the image processing system, at least one portion from each intermediate image of the plurality of intermediate images;
 assembling, by the image processing system, the extracted portions from the plurality of intermediate images to form a final image that corresponds to the formed image from the objective;
 evaluating the final image to determine acceptability of the objective; and
 rejecting the objective when the image processing system determines that the final image is not acceptable and thereafter repairing the objective.

10. The method of claim 9, wherein acquiring the plurality of intermediate images includes positioning the camera at the plurality of different positions along the optical axis.

11. The method of claim 9, wherein the image capture system comprises at least one optical component, and the acquiring the plurality of intermediate images includes positioning the camera and the at least one optical component at the plurality of different positions along the optical axis.

12. The method of claim 11, wherein the positioning the camera and the at least one optical component includes moving the camera and the at least one optical component in tandem.

13. The method of claim 9, wherein the acquiring the plurality of images includes:
 moving the image capture system to a position along the optical axis;
 acquiring, with the image capture system, an intermediate image of the formed image at the position along the optical axis; and
repeating the steps of moving the image capture system and acquiring the intermediate image until a predetermined number of intermediate images are acquired.

14. The method of claim 9, wherein the extracting at least one portion from each intermediate image include extracting an in focus portion of each intermediate image.

15. The method of claim 14, wherein the in focus portion of each intermediate image is based on the location of the image capture system along the optical axis when acquiring the intermediate image.

16. The method of claim 14, wherein identifying an in focus portion of an intermediate image includes identifying at least one of an area of higher spatial frequencies or intensity maxima from a sharpness detection algorithm.

17. The method of claim 9, further comprising:
 positioning the objective and the image capture system in an enclosure; and
 preventing, with the enclosure, ambient light from reaching the image capture system during the acquiring of the plurality of intermediate images.

18. The system of claim 7, wherein the target is a singular target that makes up the whole field of view of the objective.

19. The method of claim 16, wherein identifying at least one of an area of higher spatial frequencies or intensity maxima from a sharpness detection algorithm further comprises utilizing Sobel matrix operators for local gradients to identity the area of higher of higher spatial frequencies.

20. The system of claim 1, wherein capturing the plurality of intermediate images of the formed image from the objective further comprises moving the image capture system along the optical axis without moving the objective of the endoscope.

21. The method of claim 9, wherein acquiring the plurality of intermediate images further comprises moving the image capture system without moving the endoscope objective.

22. A method of evaluating of an objective of an endoscope, the method comprising:
 forming an image of a target with an endoscope objective, wherein the objective is apart from the endoscope, the formed image including a curved focal plane;
 relaying the formed image onto a camera of an image capture system, wherein the relayed formed image includes the curved focal plane,
 acquiring with the image capture system, a plurality of intermediate images from the formed image at a plurality of positions along an optical axis of the objective by moving the image capture system along the optical axis without moving the endoscope objective, wherein each intermediate image of the plurality of intermediate images corresponds to a different image plane with respect to the optical axis taken from the curved focal plane;
 providing, by the image capture system, the plurality of intermediate images to an image processing system;

extracting, by the image processing system, at least one portion from each intermediate image of the plurality of intermediate images;

assembling, by the image processing system, the extracted portions from the plurality of intermediate images to form a final image that corresponds to the formed image from the objective; and evaluating the final image to determine acceptability of the objective.

* * * * *